United States Patent [19]

Aloisio et al.

[11] Patent Number: 5,248,594
[45] Date of Patent: Sep. 28, 1993

[54] IMMUNODIAGNOSTIC REAGENT SPECIFIC FOR LEGIONELLA

[75] Inventors: Carol H. Aloisio, Norcross; George M. Carlone, Stone Mountain; Bonnie B. Plikaytis, Tucker; Jackie Sampson, College Park, all of Ga.

[73] Assignee: The United States of America as represented by the Department of Health and Human Services, Washington, D.C.

[21] Appl. No.: 548,011

[22] Filed: Jul. 5, 1990

[51] Int. Cl.$^5$ .................... G01N 33/569; C07K 15/28
[52] U.S. Cl. ............................. 435/7.32; 435/240.27; 435/960; 435/975; 436/518; 436/804; 530/388.4
[58] Field of Search ............... 435/7.32, 172.2, 240.27; 436/548; 530/387, 388.4

[56] References Cited

U.S. PATENT DOCUMENTS 4,931,547  6/1990  Hoffman et al. .................... 530/387

FOREIGN PATENT DOCUMENTS 364971  4/1990  European Pat. Off. ........... 435/7.32

OTHER PUBLICATIONS

K. K. Sethi, "Monoclonal Antibodies Against Legionella pneumophila Serogroup 1 Antigens: Characterization and Their Potential Applications" in Monoclonal Antibodies Against Bacteria, pp. 121–136 (1985).

Helsel et al, Current Microbiology vol. 16: 201–208 (1988).

Plikaytis et al, "Purified 60-Kilodalton Legionella Protein Antigen with Legionella-Specific and Nonspecific Epitopes", J. Clin. Microbiol. 25(11) pp. 2080–2084 (Nov. 1987).

Nowinski et al, "Monoclonal Antibodies for Diagnosis of Infectious Diseases in Humans", Science 219 pp. 637–644 (11 Feb. 1983).

Edelstein, "Legionella" in Manual of Clinical Microbiology, 4th Ed. pp. 373–381 (1985).

Primary Examiner—Esther L. Kepplinger
Assistant Examiner—Carol E. Bidwell
Attorney, Agent, or Firm—Lowe, Price, LeBlanc & Becker

[57] ABSTRACT

A set of three unique monoclonal antibodies have been produced which recognize Legionella with particular specificity, without substantial cross-reactivity with non-Legionella bacteria. These monoclonal antibodies are useful as immunodiagnostic reagents for detecting Legionella.

9 Claims, 1 Drawing Sheet

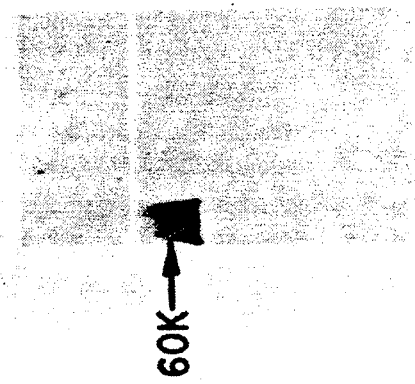
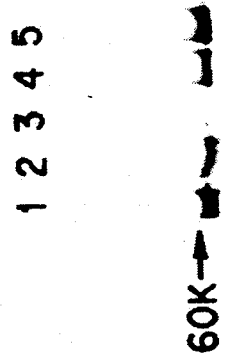
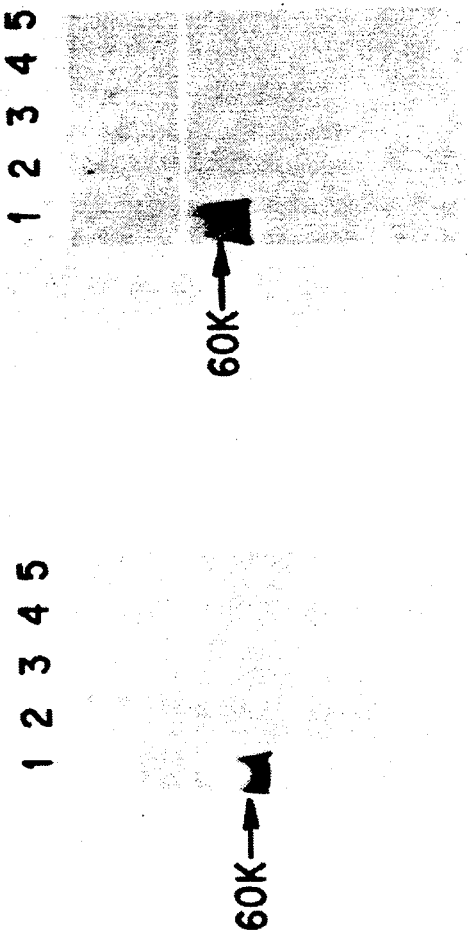
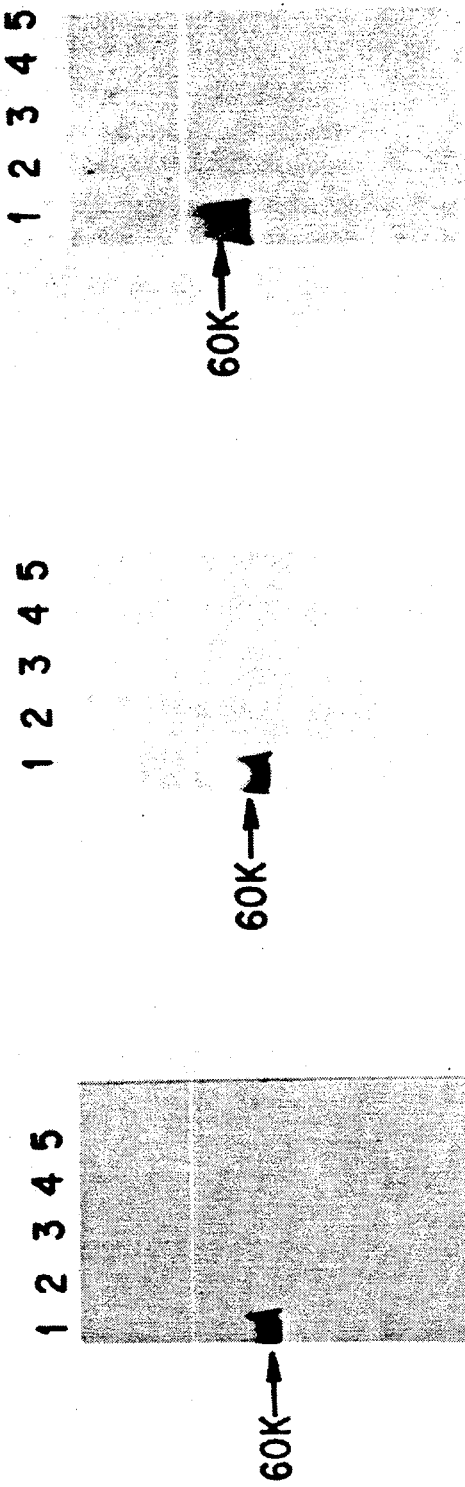

IMMUNODIAGNOSTIC REAGENT SPECIFIC FOR LEGIONELLA

The present invention is related generally to immunodiagnostic reagents. More particularly, the present invention is related to novel monoclonal antibodies for genus wide detection specifically of Legionella species.

BACKGROUND OF THE INVENTION

Currently, there are about 30 recognized species containing 47 serogroups of Legionella. Present serological detection methods are based on about 48 serogroup specific antigens which require about 48 serogroup specific antisera. Sampson et al. (J. Clin. Micro., 23:92-99, 1986) described a 58-kilodalton (later 60-kilodalton) protein antigen that was present in all Legionella species examined and which was found to be immunogenic in humans, reacting with serum from 100% of the culture-confirmed cases of legionellosis that were tested. Antibody to this protein was considered as a possible probe in immunological procedures to detect all species in the genus Legionella. Polyclonal rabbit antisera to the 60-kilodalton protein was produced by the method of Plikaytis et al. (J. Clin. Micro., 25:2080-2084, 1987) for use as a detection reagent. To achieve specificity to the Legionella genus, the polyclonal antisera had to be sequentially absorbed with three heterologous organisms, thereby significantly decreasing the potency of the antisera. In contrast, the monoclonal antibodies produced by the hybridoma cell lines are not subject to the variabilities encountered in the production of polyclonal antisera.

A variety of diagnostic techniques for detection of Legionnaire's disease are known. Patent No. 87/05609 issued to Hoffman describes monoclonal antibodies for the detection of Legionella species. However, these antibodies have cross-reactivity with the bacteria of other genus.

SUMMARY OF THE INVENTION

It is, therefore, an object of the present invention to provide a set of at least three monoclonal antibodies which, in combination, recognize all known species of Legionella without substantial cross-reactivity with other bacteria with which heretofore known monoclonal antibodies exhibit significant cross-reactivity.

It is another object of the present invention to provide novel immunodiagnostic reagents for differentially detecting the presence of bacteria belonging to the genus of Legionella in biological or environmental samples and the like.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIGS. 1A-1D show binding specificity of Hoffman's monoclonal antibody and the claimed monoclonal antibodies with the 60 kDa protein among non-Legionella bacteria using Western blot analysis. Blots were probed with Hoffman's monoclonal antibody GW2X4B8B2H6 (A), Aloisio's monoclonal GB5BE8 (B), GB5AF6 (C), and CA4AF5 (D). Lane 1 contains a positive control strain of *L. pneumophila* serogroup 1; 2, *Acinetobacter lwoffii*; 3, *Pseudomonas aeruginosa*; 4, *Bordetella bronchiseptica*; and 5 *B. pertussis*. Note the strong reactivity in lanes 2, 4, and 5 with *Acinetobacter*, *B. bronchiseptica*, and *B. pertussis* when probed with the Hoffman antibody.

DETAILED DESCRIPTION OF THE INVENTION

The above and various other objects and advantages of the present invention are achieved by producing a set of three stable hybridoma clones such that each clone secretes sufficient amount of uniformly specific monoclonal antibodies which bind to specific antigenic sites (isotypic epitopes) unique to the 60-kilodalton protein of *Legionella*. These three monoclonal antibodies obtained in accordance with the present invention are designated herein as GB5BE8, GB5AF6 and CA4AF5.

A deposit of the three hybridomas secreting monoclonal antibodies GB5BE8, CA4AF5 and GB5AF6 has been made at the ATCC, Rockville, Md., on May 23, 1990, Apr. 24, 1990 and May 10, 1990, respectively under accession numbers HB 10459, HB10439 and HB10453, respectively. The deposit shall be viably maintained, replacing if it becomes non-viable during the life of the patent, for a period of 30 years from the date of the deposit, or for 5 years from the last date of request for a sample of the deposit, whichever is longer and, upon issuance of the patent, made available to the public without restriction in accordance with the provisions of the law. The Commissioner of Patents and Trademarks, upon request, shall have access to the deposit.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "substantial" cross reactivity as defined herein means significant or considerable amount of cross reactivity.

MATERIALS AND METHODS

Purified 60-kilodalton protein antigen was produced from *Legionella pneumophilia* serogroup-1. A highly enriched extract was produced by ultracentrifugation. Further purification was carried out by standard affinity chromatography and ion exchange high performance liquid chromatography. For initial immunization, a dosage of 20 micrograms of purified protein in phosphate buffered saline with incomplete Freund's adjuvant was administered to mice. This was repeated at 6 weeks. One week later, the animal was given 10 micrograms purified protein intravenously on two consecutive days. The general procedures of Kohler and Milstein (Nature, 256, 1975) were used as modified by Zola and Brooks (Monoclonal Antibodies: Techniques and Applications, J. G. R. Hurrell (ed.), CRC Press, Boca Raton, pp. 1-57, 1982). Immunized mice and antibody from hybridized cells were screened for reactivity by standard Western blot analysis using purified 60-kilodalton protein as the antigen and goat anti-mouse horseradish peroxidase conjugate. From numerous clones tested, three clones were isolated that exhibited the desired reactivity. Further analysis of the three clones was done using standard SDS-PAGE followed by immunoblots on 42 Legionella serogroups (23 species) and 62 non-Legionella bacterial strains; the results are shown in Table 1. The results indicate that the three hybridoma cell lines produce monoclonal antibody that, in combination, react with all tested strains of Legionella.

It should be noted that there was no reactivity with the five strains of Bordetella and one strain of Acinetobacter tested by Western blot analysis. This is a significant difference from the reactivity of the GW2X4B8B2H6 monoclonal antibody reported by Hoffman. Hoffman reported that this antibody reacts strongly with 12 strains of Bordetella and one strain of Acinetobacter when tested in an ELISA method. In comparative tests presented herein, it was found that the GW2X4B8B2H6 antibody strongly reacted with the Bordetella and Acinetobacter species in Western blot analysis (FIG. 1). This is quite significant since a monoclonal antibody or pool of monoclonal antibodies that detect most Legionella species without substantial cross-reactivity with non-Legionella species would provide an important screening tool for both clinical and environmental samples. Clearly, the strong cross-reactivity of the Hoffman monoclonal antibody makes it unfit for this type of application due to unacceptable cross-reactivity. The strong cross-reactivity of the GW2X4B8B2H6 Hoffman antibody and the lack of this cross-reactivity in the monoclonal antibodies reported herein indicate that even though these antibodies react to the same 60-kDa protein, the epitope specificity is distinctly different.

The unique monoclonal antibodies of the present invention now provide a reliable, rapid, simple and specific diagnostic test for Legionella. The method comprises reacting a sample suspected of Legionella infection with a part (reactive fragment) or whole of the monoclonal antibodies of the present invention, a positive immunological reaction being indicative of the presence of Legionella bacterium in the sample. Such immunodiagnostic tests, which include immunohistochemical, immunoblotting, radioimmunoassay and the like, are quite routine and standard and well known to one of ordinary skill in the art. A diagnostic kit or an immunodiagnostic reagent in accordance with the present invention comprises containers containing an immunoreactive amount of the monoclonal antibodies of the present invention, either alone or as a combined mixture in a sterile, non-toxic medium such as a buffered solution and the like.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

| SPECIFICITY OF LEGIONELLA 60K MONOCLONALS | | | | | |
|---|---|---|---|---|---|
| Bacteria | Serogroup | Strain ID | GB5 BE8 | GB5 AF6 | CA4 AF5 |
| Legionella pneumophila | 1 | Philadelphia 1 | + | + | + |
| Legionella pneumophila | 2 | Togus 1 | + | + | + |
| Legionella pneumophila | 3 | Bloomington 2 | + | + | + |
| Legionella pneumophila | 4 | Portland 1 | + | + | + |
| Legionella pneumophila | 5 | Cambridge 2 | + | + | + |
| Legionella pneumophila | 6 | Chicago 2 | + | + | + |
| Legionella pneumophila | 7 | Chicago 8 | + | + | + |
| Legionella pneumophila | 8 | Concord 3 | + | + | + |
| Legionella pneumophila | 9 | In-23-G2-C2 | + | + | + |
| Legionella pneumophila | 10 | Leiden 1 | + | + | + |
| Legionella pneumophila | 11 | 797-PA-H | + | + | + |
| Legionella pneumophila | 12 | 570-CO-H | − | + | + |
| Legionella pneumophila | 13 | 82A3105 | +/− | + | + |
| Legionella pneumophila | 14 | 1169-MN-H | +/− | + | + |
| Legionella bozemanii | 1 | WIGA | + | + | + |
| Legionella bozemanii | 2 | Toronto 3 | − | +/− | +/− |
| Legionella dumoffii | 1 | NY-23 | +/− | + | − |
| Legionella gormanii | 1 | LS-13 | + | + | +/− |
| Legionella micdadei | 1 | Tatlock | +/− | + | + |
| Legionella longbeachae | 1 | Long Beach 4 | + | + | +/− |
| Legionella longbeachae | 2 | Tucker 1 | + | + | +/− |
| Legionella jordanis | 1 | BL-540 | + | + | +/− |
| Legionella oakridgensis | 1 | Oak Ridge 10 | − | − | + |
| Legionella wadsworthii | 1 | 81-716 | + | + | − |
| Legionella feeleii | 1 | WO-44C-C3 | − | − | + |
| Legionella feeleii | 2 | 691-WI-H | − | − | + |
| Legionella sainthelensi | 1 | Mt.St.Helen 4 | + | + | + |
| Legionella anisa | 1 | WA-316-C3 | + | + | +/− |
| Legionella santicrucis | 1 | SC-63-C7 | − | + | + |
| Legionella steigerwaltii | 1 | SC-18-C9 | + | + | +/− |
| Legionella parisiensis | 1 | PF-209C-C2 | + | + | + |
| Legionella spiritensis | 1 | Mt.St.Helen 9 | + | + | + |
| Legionella hackeliae | 1 | Lansing 2 | − | − | +/− |
| Legionella hackeliae | 2 | 798-PA-H | − | − | +/− |
| Legionella maceachernii | 1 | PX-1-G2-E2 | +/− | +/− | + |
| Legionella jamestowniensis | 1 | JA-26-G1-E2 | +/− | + | + |
| Legionella cherrii | 1 | ORW | + | + | +/− |
| Legionella rubrilucens | 1 | WA-270A-C2 | + | + | + |
| Legionella erythra | 1 | SE-32A-C8 | +/− | +/− | − |

TABLE 1-continued
SPECIFICITY OF LEGIONELLA 60K MONOCLONALS

| Bacteria | Serogroup | Strain ID | GB5 BE8 | GB5 AF6 | CA4 AF5 |
|---|---|---|---|---|---|
| Legionella israelensis | 1 | Bercovier 4 | − | − | + |
| Legionella birminghamensis | 1 | 1407-AL-H | +/− | +/− | + |
| Legionella cincinnatiensis | 1 | 72-OH-H | + | + | +/− |
| Pseudomonas testosteroni | | KC1765 | − | − | − |
| Yersinia pseudotuberculosis | | 514-84 | − | − | − |
| Shigella sonnei | 0 | 85 | − | − | − |
| Pseudomonas aeruginosa | | 5 | − | − | − |
| Streptococcus pneumoniae | | Pn-1 | − | − | − |
| Pseudomonas maltophilia | | KC1768 | − | − | − |
| Bordetella bronchisepta | | F6286 | − | − | − |
| Bordetella bronchisepta | | F6287 | − | − | − |
| Pseudomonas diminuta | | KC1797 | − | − | +/− |
| Pseudomonas cepacia | | KC1766 | − | − | − |
| Serratia marcescens | | 4391-83 | − | − | − |
| Escherichia coli | | 16 | − | − | − |
| Serratia marcescens | | 4391-83 | − | − | − |
| Escherichia coli | | 16 | − | − | − |
| Hemophilus influenzae a | | KC818 | − | − | − |
| Pseudomonas fluorescens | | CDC93 | − | − | − |
| Escherichia coli | | 013 | − | − | − |
| Klebsiella ascorbata | | 426-84 | − | − | − |
| Escherichia fergusonii | | 1295-83 | − | − | − |
| Shigella flexneri | | 37 | − | − | − |
| Staphylococcus aureus | | 42BP | − | − | − |
| Yersinia enterocolitica | | 1149-84 | +/− | +/− | − |
| Hemophilus influenzae e | | KC528 | − | − | +/− |
| Hemophilus influenzae b | | 1179-85 | − | − | +/− |
| Pseudomonas aeruginosa | | 2 | − | − | − |
| Pseudomonas aeruginosa | 0 | 8 | − | − | − |
| Klebsiella oxytoca | | 4698-84 | − | − | − |
| Escherichia hermanii | | 460-84 | − | − | − |
| Providencia stuartii | | 4007-83 | − | − | − |
| Providencia rettgeri | | 5317-81 | − | − | − |
| Enterobacter aerogenes | | 1942-81 | − | − | − |
| Alcaligenes faecalis | | | − | − | − |
| Acinetobacter lwoffii | | mima | − | − | − |
| Klebsiella pneumoniae | | 4809-84 | − | − | − |
| Pseudomonas paucimobilis | | B3271 | − | − | − |
| Bordetella pertussis | | F6324 | − | − | − |
| Bordetella pertussis | | F6323 | − | − | − |
| Pseudomonas alcaligenes | | ABB50 | − | − | − |
| Pseudomonas acidovorans | | KC1769 | − | − | − |
| Neisseria meningitidis | C | KC792 | − | − | − |
| Pseudomonas fluorescens | | E.B. | − | − | − |
| Bordetella parapertussis | | E1142 | − | − | − |
| Flavobacterium meningosepticum | 0 | 698 | − | − | − |
| Listeria monocytogenes | | KC1775 | − | − | − |
| Listeria monocytogenes | | KC2380 | − | − | − |
| Listeria innocua | | KC1783 | − | − | − |
| Listeria innocua | | KC1784 | − | − | − |
| Streptococcus pyogenes | | SS482 | − | − | − |
| Streptococcus pyogenes | | SS91 | − | − | − |
| Campylobacter jejuni | | D133 | +/− | +/− | − |
| Campylobacter jejuni | | L1 | +/− | +/− | − |
| Campylobacter jejuni | | L2 | +/− | +/− | − |
| Campylobacter jejuni | | L9 | +/− | +/− | − |
| Campylobacter fetus | | D223 | − | − | − |
| Campylobacter fetus | | D373 | − | +/− | − |
| Campylobacter fetus | | D406 | − | − | − |
| Campylobacter fetus | | D411 | − | − | − |
| Vibrio cholerae | | 01 Inata | − | − | − |
| Salmonella typhimurium | | 2489-88 | − | − | − |
| Clostridium difficile | 0 | 880-221 | − | − | − |
| Clostridium perfringens | | 860386 | − | − | − |
| Clostridium septicum | | 70426 | − | − | − |
| Streptococcus salivarius | | SS908 | − | − | − |
| Streptococcus salivarius | | SS1062 | − | − | − |

What is claimed is:

1. A monoclonal antibody selected from the group consisting of the monoclonal antibodies GB5BE8 produced by hybridoma ATCC HB10459, GB5AF6 produced by hybridoma ATCC HB10453, CA4AF5 produced by hybridoma ATC HB10439, and mixtures thereof, said monoclonal antibody having binding specificity for detection of Legionella species.

2. The monoclonal antibody of claim 1, which is GB5BE8 produced by hybridoma ATCC HB10459.

3. The monoclonal antibody of claim 1, which is GB5AF6 produced by hybridoma ATCC HB10453.

4. The monoclonal antibody of claim 1, which is CA4AF5 produced by hybridoma ATCC HB10439.

5. A polyvalent mixture of monoclonal antibodies comprising GB5BE8 produced by hybridoma ATCC HB10459, GB5AF6 produced by hybridoma ATCC HB10453, CA4AF5 produced by hybridoma ATCC HB10439, said mixture in combination reacting with the strains of Legionella as set forth in Table 1.

6. An immunodiagnostic reagent for detecting Legionella, comprising an immunoreactive amount of a monoclonal antibody of claim 1 in a vehicle.

7. An immunodiagnostic reagent according to claim 6, wherein the vehicle is a sterile, non-toxic medium.

8. A method for screening sample to detect a Legionella species, comprising contacting a sample suspected of being infected with Legionella with a monoclonal antibody selected from the group consisting of GB5BE8 produced by hybridoma ATCC HB10459, GB5AF6 produced by hybridoma ATCC HB10453, CA4AF5 produced by hybridoma ATCC HB10439, and mixtures thereof, and detecting specific binding of said monoclonal antibody to the sample, wherein a positive specific binding reaction is indicative of the presence of Legionella in said sample, said method not being positively effective to detect *Legionella bozemanii* strain Toronto 3, *Legionella hackeliae* strain Lansing 2 or strain 798-PA-H.

9. A method according to claim 8, wherein screening is carried out by an immunohistochemical test, an immunoblotting test, or a radioimmunoassay test.

* * * * *